April 5, 1960

M. J. MURRAY

MINT PLANT

Filed June 8, 1959

Plant Pat. 1,926

INVENTOR.
MERRITT J. MURRAY

BY Lindley E. Miller

United States Patent Office

Plant Pat. 1,926
Patented Apr. 5, 1960

1,926

MINT PLANT

Merritt J. Murray, Kalamazoo, Mich., assignor to A. M. Todd Company, Kalamazoo, Mich., a corporation of Michigan Application June 8, 1959, Serial No. 818,986

1 Claim. (Cl. 47—59)

Figure 1:
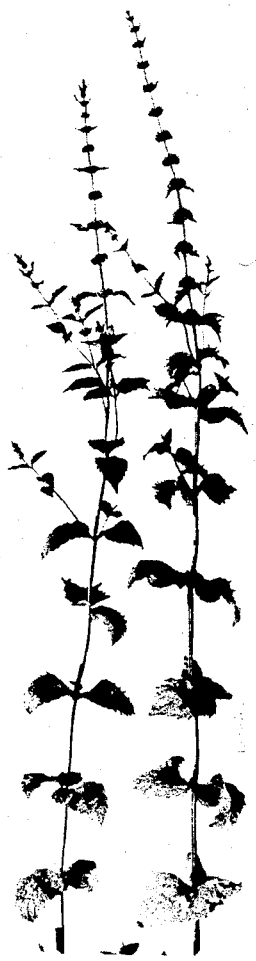

This invention relates to a new and distinct variety of mint plant which was initially produced by hybridization between *Mentha arvenis* L. var. *piperascens* Briq. and *Mentha crispa* L. (*Mentha spicata* L. var. *crispata*) and thereafter asexually reproduced from stolons at nurseries near Kalamazoo, Michigan. Although the variety of Plant Patent No. 1,614 and the variety of concurrently filed co-pending plant patent application Serial No. 818,987 resulted from the same cross, it will be apparent as the description proceeds that the variety described in this application is distinct from either of the other two varieties mentioned.

The new variety is characterized by its more erect habit and stronger stems and its tendency to grow somewhat taller than either *Mentha arvensis* L. var. *piperascens* Briq. or *Mentha crispa* L. or the variety of Plant Patent No. 1,614, the plants often growing to a height of three and one-half feet, or more, under Washington field conditions. The plants are medium branched and the stems are coarser than those of *Mentha crispa* L., the plant being less fragile than *Mentha arvensis* L. var. *piperascens* Briq. The new variety is hardy under southern Michigan and central Washington conditions. The colors of the plant and flowers are not distinctive and resemble closely those of other common mint varieties when grown under comparable conditions.

The leaves of the new variety are opposite, deeply serrated with sharply pointed serrations, medium rather than broadly ovate and are often wrinkled and curled to some extent although not as much as the leaves of the variety of Plant Patent No. 1,614. The wrinkling and curling of the leaves are more apparent on the full grown leaves than on the partially developed leaves, the variety differing significantly in this respect from the variety of Plant Patent No. 1,614. The leaves are on the average somewhat larger than those of the variety of Plant Patent No. 1,614. The leaves are only very slightly hairy on the under sides of the ribs while the stems are smooth with few sparse hairs.

The flowers are borne in the form of axillary globular clusters principally on a single spike although a few flowers may be borne near the ends of branches from the central spike, the variety differing significantly in this respect from the full-flowered branch spikes of the variety of co-pending plant patent application Serial No. 818,987. The leaves on the flower spikes are much larger than the leaves on the flower spikes of the variety of Plant Patent No. 1,614, the leaves adjacent to the lowermost axillary flower clusters often being approximately one-half their eventual full length by the time the flowers open.

The new variety is highly resistant to Verticillium wilt, *Verticillium albo-atrum* R. & B. var. *menthae* Nelson, nearly immune to spearmint rust, frequently identified as *Puccinia menthae* Pers., and only very slightly susceptible to powdery mildew, *Erysiphe cichoracearum* D.C., and to leaf spot diseases, including *Cephalosporium sp.*, which attack *Mentha arvensis* L. var. *piperascens* Briq.

The resistance of the new variety against these organisms was demonstrated on muck and upland soil near Mentha, Michigan. Disease conditions were accentuated by interplanting plots of the new variety with plots of *Mentha arvensis* L. var. *piperascens* Briq., *Mentha citrata* Ehrh., *Mentha piperita* L. *Mentha cardiaca* (Gerarde or Baker?), *Mentha spicata* L. and other wild species as well as of a number of susceptible hybrid varieties under test. The mildew conditions were accentuated by spreading greenhouse grown *Mentha arvensis* L. var. *piperascens* Briq. plants heavily infested with powdery mildew over the plots. The first year's plots were left unplowed, the plants in them being permitted to grow undisturbed the next year to furnish additional continuing inoculation of newly planted plots.

Susceptible varieties, including *Mentha arvensis* L. var. *piperascens* Briq., were heavily infested with leaf spot diseases, powdery mildew, spearmint rust and Verticillium wilt on the plots on muck soil and with all of these diseases except Verticillium wilt on the splots on upland soil. The new variety was not affected appreciably by Verticillium wilt and was essentially immune to spearmint rust. It was infested somewhat more, but not with any appreciable damage, by powdery mildew and leaf spot diseases.

Similar test procedures as regards mildew and leaf spot diseases were carried out on volcanic mineral soil near Yakima, Washington, under conditions of ditch irrigation with comparable results.

The new variety is particularly remarkable for its resistance to Verticillium wilt and spearmint rust, for the high total menthol content of its oil and especially for the low proportion of the total menthol which occurs in the oil in the form of esters. The oil of the new variety usually contains from 82 to 86 percent, or higher, of total menthol as determined by the method for total menthol content given in the United States Pharmacopoeia No. 14. This is all the more remarkable since one of the parents, *Mentha crispa* L., is a wild spearmint, the oil of which contains little or no menthol. The proportion of the total menthol present in the oil of the new variety in the form of esters is generally considerably below 8 percent and is often as low as 4.7 percent, depending apparently upon the conditions under which the plant is grown. This is in marked contrast to the oil from the variety of Plant Patent No. 1,614 in which the proportion of total menthol occurring in the form of esters is much greater and much more erratic, often varying between 15 and 30 percent.

Figure 2:
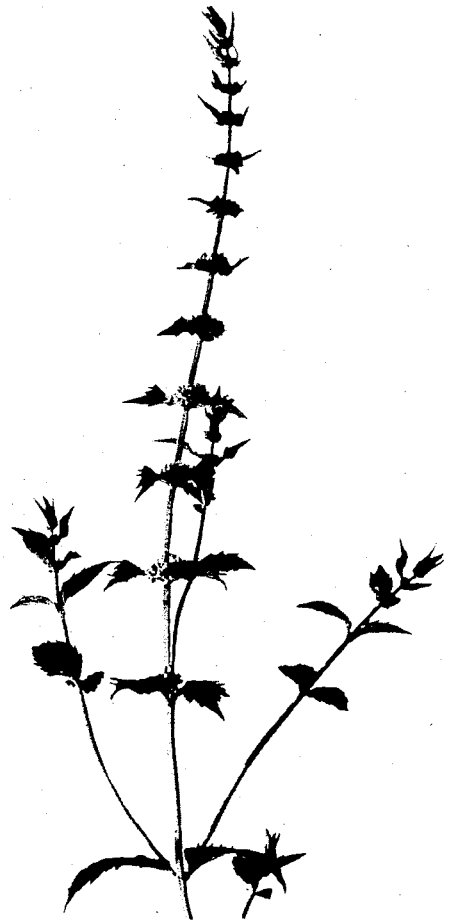

In the drawings, which are photographic illustrations of the new variety:

Figure 1 is a view of a pair of representative branches of the new variety showing the general arrangement and form of the leaves, stems and flowers, and Figure 2 is an enlarged view of a flower stem showing the relationship of the flowers and adjacent leaves.

The hybridization leading to the new variety was carried out in the summer of 1951 in southern Michigan. The seed resulting from the hybridization was planted and grown in the spring and summer of 1952. The new variety was selected from among a large number of other hybrids as being of commercial value because of the exceptionally high total menthol content of its oil, because of the consistently low proportion of the total menthol in the oil which is in the form of esters and because of its more erect habit and stronger stems as compared with the variety of Plant Patent No. 1,614. The new variety was first asexually reproduced in the spring of 1953 near Kalamazoo, Michigan, and in central Washington. It has been grown since 1953 by asexual reproduction from stolons in southern Michigan. It has also been grown since 1953 by asexual reproduction from stolons part of the time in central Washington and part of the time in north central Oregon. It has consistently exhibited its characteristics of erect habit, tall growth and strong stems together with the high total menthol content of its oil and the low proportion of the menthol in the oil in the form of esters.

I claim:

A new and distinct variety of mint plant substantially as described, characterized particularly by its erect habit, tall growth, strong stems and its only moderately curled leaves as compared with the variety of Plant Patent No. 1,614, by its high resistance to attack by *Verticillium albo-atrum* R. & B. var. *menthae* Nelson and spearmint rust, frequently identified as *Puccinia menthae* Pers., by the high total menthol content of its oil and by the exceptionally low proportion of the total menthol content of its oil occurring in the form of esters.

No references cited.